US006886387B1

United States Patent
Lin et al.

(10) Patent No.: US 6,886,387 B1
(45) Date of Patent: May 3, 2005

(54) BRUSH PRESSURE CALIBRATION APPARATUS AND METHOD

(75) Inventors: Ching-Long Lin, Hsinchu (TW); Yung-Hsiang Hu, Hsinchu (TW); Fu-Tao Ho, Hsinchu (TW)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 0 days.

(21) Appl. No.: 10/834,769

(22) Filed: Apr. 28, 2004

(51) Int. Cl.$^7$ .............................................. G01N 19/02
(52) U.S. Cl. ............................................ 73/9; 73/1.79
(58) Field of Search ...................................... 73/9, 1.79

(56) References Cited

U.S. PATENT DOCUMENTS

| | | | | |
|---|---|---|---|---|
| 3,625,036 A | * | 12/1971 | Fapiano ........................ 72/9.3 |
| 4,888,717 A | * | 12/1989 | Ditto et al. .................. 700/302 |
| 5,689,092 A | * | 11/1997 | Wurz et al. .................. 177/145 |
| 5,961,372 A | * | 10/1999 | Shendon ....................... 451/41 |
| 6,336,851 B1 | * | 1/2002 | Shendon ...................... 451/303 |
| 6,547,903 B1 | * | 4/2003 | McNichols et al. ............ 156/64 |
| 6,558,602 B1 | * | 5/2003 | Melbye et al. ............... 264/280 |
| 6,561,870 B2 | * | 5/2003 | Saldana et al. ................ 451/10 |
| 6,620,270 B2 | * | 9/2003 | Ehlert et al. ................... 156/64 |
| 6,635,212 B1 | * | 10/2003 | Melbye et al. ............... 264/167 |
| 6,773,332 B2 | * | 8/2004 | Moore ........................... 451/5 |
| 6,783,440 B2 | * | 8/2004 | Togawa et al. ............... 451/56 |
| 2004/0101704 A1 | * | 5/2004 | Hermans et al. ............ 428/535 |

FOREIGN PATENT DOCUMENTS

EP          491234 A2 *  6/1992          .......... G01N/19/02

* cited by examiner

*Primary Examiner*—Hezron Williams
*Assistant Examiner*—John Fitzgerald
(74) *Attorney, Agent, or Firm*—Tung & Associates

(57) ABSTRACT

A novel apparatus and method for calibrating the gap distance between adjacent scrubber brushes with the frictional force of the brushes against a wafer, is disclosed. The apparatus includes a support frame, at least one pair of load cells carried by the support frame, at least one test plate operably engaging the load cells, and at least one electronic indicator operably connected to the load cells, respectively, for indicating a force exerted on the load cells by the test plate. The method includes placing at least one test plate between the adjacent scrubber brushes, rotating the scrubber brushes against the test plate, determining the frictional force of each brush against the plate, and adjusting the gap distance between the brushes to obtain a desired frictional force for the scrubber cleaning of production wafers.

20 Claims, 3 Drawing Sheets

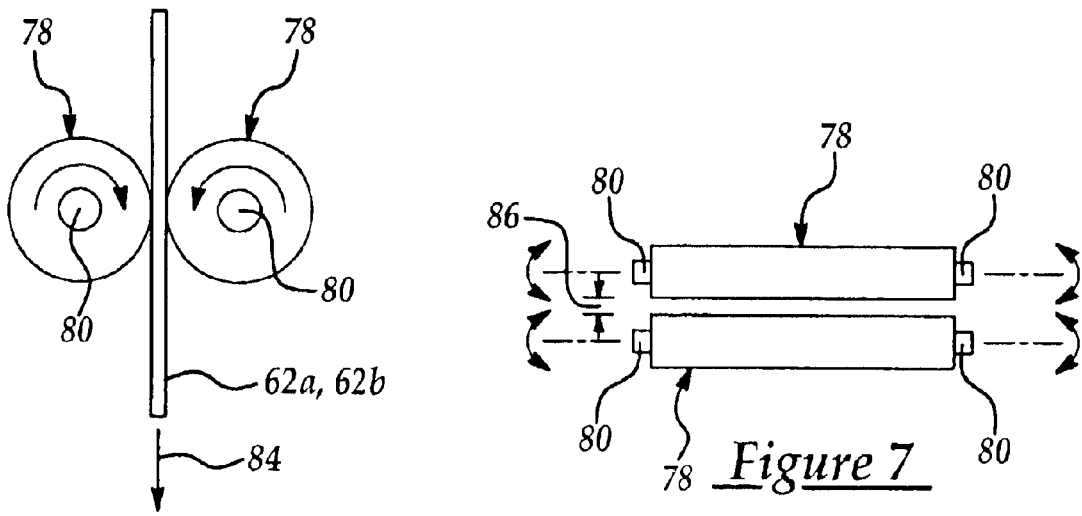
*Figure 6*
*Figure 7*
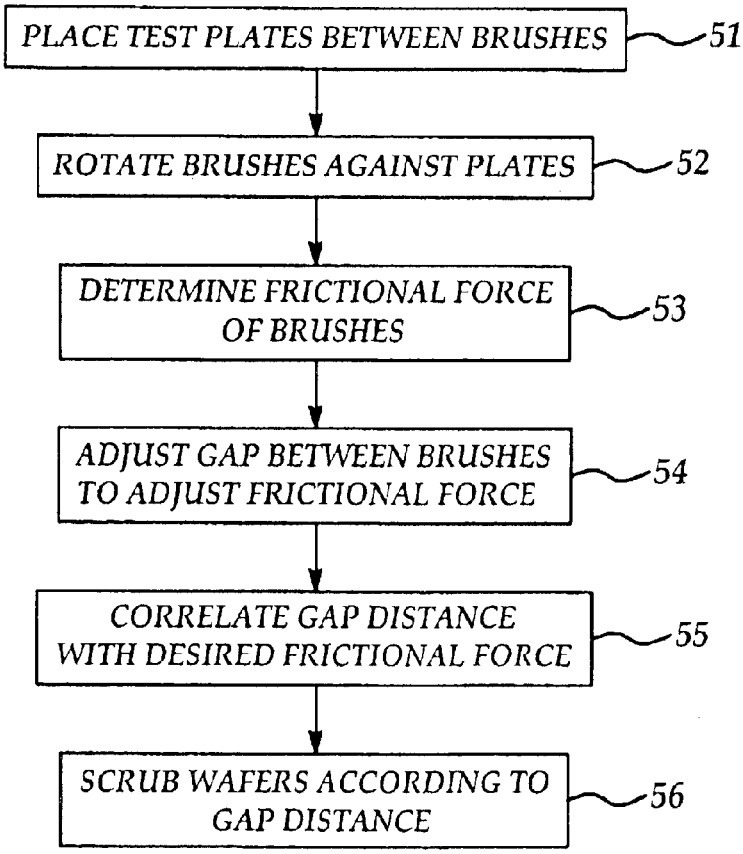
*Figure 8*

BRUSH PRESSURE CALIBRATION APPARATUS AND METHOD

FIELD OF THE INVENTION

The present invention relates to scrubber cleaners used in the cleaning of semiconductor wafer substrates particularly after a CMP process. More particularly, the present invention relates to a novel apparatus and method for calibrating the frictional force of scrubber brushes against a wafer with the brush gap distance.

BACKGROUND OF THE INVENTION

In the fabrication process for semiconductor devices, numerous fabrication steps, as many as several hundred, must be executed on a silicon wafer in order to complete integrated circuits on the wafer. Generally, the process for manufacturing integrated circuits on a silicon wafer substrate typically involves deposition of a thin dielectric or conductive film on the wafer using oxidation or any of a variety of chemical vapor deposition processes; formation of a circuit pattern on a layer of photoresist material by photolithography; placing a photoresist mask layer corresponding to the circuit pattern on the wafer; etching of the circuit pattern in the conductive layer on the wafer; and stripping of the photoresist mask layer from the wafer. The wafer is typically subjected to a polishing operation to provide an extremely level starting surface on the wafer.

During the subsequent structuring of the substrate, the various processing steps are used to build up layers of conductors and dielectrics, for example, on which other layers are formed to fabricate the circuits. With structuring becoming ever finer, the associated replication processes are becoming more sensitive to surface variations on the substrate. Therefore, it has now become necessary to "re-level" the wafer surface even while production of the integrated circuits are in progress. The re-leveling operation is referred to as planarizing and is typically accomplished using the CMP (chemical mechanical planarization) method using a chemical mechanical polishing process.

In chemical mechanical polishing, an abrasive suspension agent or slurry is dispensed onto a polishing surface. Relative movement between the polishing surface and the wafer produces a combined mechanical and chemical effect on the surface of the wafer. This process creates a highly level surface on the wafer. In order to remove the still-moist remains of slurry, as well as small surface defects which may remain in the wafer and disrupt the otherwise planar continuity of the wafer surface after the CMP process, post-CMP cleaning steps are required.

One of the cleaning steps carried out after the chemical mechanical polishing process is facilitated using rotating scrubber brushes which are actuated inside a scrubber cleaner. Accordingly, a special washing fluid and a rotational movement with multiple pairs of scrubber brushes can clean both sides of the wafer using contact pressure against the wafer. Because the wafer becomes considerably more valuable with each successive planarizing operation, the post-CMP brush cleaning operation is commercially significant.

One of the most common post-CMP scrubber cleaners used to remove residues from a wafer substrate after a CMP operation is the MIRRA MESA brush scrubber cleaner. The MIRRA MESA brush scrubber cleaner cleans wafers using a combination of rinsing, megasonic rinsing, and brush cleaning. The wafer substrates, having been previously subjected to chemical mechanical planarization, are loaded into a wet environment, typically water, and then transported through a series of cleaning chambers for the brush cleaning cycle. The brush cleaning cycle involves rotating the wafer at a specific speed, typically about 1500 rpm, while a jet of deionized water is sprayed on the wafer to dislodge any loose debris from the CMP process. Simultaneously, the wafer is brushed with a foam brush, which rotates at typically about 400 rpm.

Referring to FIG. 1, a post-CMP wafer cleaning system 50 typically includes an input shuttle 11 which can receive multiple wafers 12, carried in a cassette 14 provided in a pod 10, from a polish unit (not shown). A walking beam (not shown) removes individual wafers 12 from the input shuttle 11 and transports the wafers 12 to a mega tank 11a, first brush station 16a, a second brush station 16b, an SRD station 20 and an output shuttle 22, step-by-step. In the first brush station 16a and second brush station 16b, each wafer 12 is scrubbed with selected chemicals and water. Next, the wafer 12 is transported to the spin, rinse and dry (SPD) station 20, where water is sprayed onto the surface of the wafer 12 as the wafer 12 is rotated at a speed of typically about 180–400 rpm, and then spun dry. Finally, the wafer 12 is transported from the SPD station 20 to the output station 22. The cleaned wafers 12 are placed in a cassette 14 provided in a pod 23 for transport of the wafers 12 to the next processing station.

A brush assembly 30, shown in FIG. 2, is provided in each of the first brush station 16a and second brush station 16b. The brush assembly 30 includes a pair of parallel, adjacent, generally cylindrical scrubber brushes 32 mounted on respective brush shafts 34. Drive motors (not shown) operably engage the brush shafts 34 to rotate each scrubber brush 32. One of the brushes 32 is typically rotated in the clockwise direction, whereas the other brush 32 is typically rotated in the counterclockwise direction.

In operation, a wafer 12 is vertically positioned between the rotating brushes 32. The brushes 32 are rotated by the drive motors (not shown) to scrub the respective sides of the wafer 12 and remove post-CMP particles from the wafer 12. Simultaneously, deionized water is typically sprayed onto both sides of the wafer 12 to wash the dislodged particles from the wafer surfaces. The frictional force of each brush 32 against the wafer 12 can typically be adjusted by outward or inward movement of the brushes 32, as indicated by the straight double-headed arrows in FIG. 2.

The post-CMP scrubber brush method for removing particles and remaining surface defects from the surface of a planarized wafer is attended by several disadvantages, one of the foremost being that the scrubber brush has a tendency to trap and become contaminated with the larger particles removed from the wafer. Consequently, the trapped particles may potentially become dislodged from the scrubber brush upon cleaning and planarization of a subsequent wafer. In the semiconductor fabrication industry, minimization of particle contamination on semiconductor wafers increases in importance as the integrated circuit devices on the wafers decrease in size. With the reduced size of the devices, a contaminant having a particular size occupies a relatively larger percentage of the available space for circuit elements on the wafer as compared to wafers containing the larger devices of the past. Moreover, the presence of particles in the integrated circuits compromises the functional integrity of the devices in the finished electronic product.

One of the solutions to the brush-induced contamination problem includes regular replacement of the scrubber brushes 32. After replacement of the brushes 32, the contact pressure of the brushes 32 must be calibrated to exert the correct frictional force of the brushes 32 against wafers 12 subsequently cleaned between the brushes 32. A typical conventional contact pressure calibration procedure for a post-CMP cleaning apparatus is shown in FIGS. 3A and 3B.

As shown in FIG. 3A, in a first step after the replacement brushes 32 are installed, the baseline contact pressure of the brushes 32 is defined as the pressure which corresponds to the position of the brushes 32 when the brushes 32 are just touching each other in the closed configuration. Accordingly, the hard-stop of the brush scrubber tool is adjusted to close the gap distance between the brushes 32, such that the bristles 33 of the brushes 32 just touch each other.

Next, as shown in FIG. 3B, in a second step the hard stop of the scrubber tool is adjusted to move the brushes 32 closer to each other until the bristles 33 of the brushes 32 are overlapping each other by 1 mm. At that point, the contact pressure of the brushes 32 is correctly calibrated for the scrubber cleaning of post-CMP wafers.

A common limitation of the brush contact pressure calibration procedure outline above is the difficulty of visually determining whether the brushes are just touching each other in the step of FIG. 3A. This is compounded by distortion of the generally cylindrical shape of the brushes during storage or replacement. In the event that the brushes are not correctly positioned with respect to each other in the step of FIG. 3A, this will result in an incorrect position of the brushes in the step of FIG. 3B. Consequently, the contact pressure, and thus, the frictional force, of the brushes against production wafers during cleaning will be either excessive or inadequate. Excessive frictional force of the brushes against the wafers tends to scratch the wafers, whereas inadequate frictional force of the brushes leads to incomplete removal of particulate contaminants from the wafers. Accordingly, a novel calibration procedure is needed for calibrating the contact pressure of scrubber brushes in a post-CMP wafer cleaner.

Accordingly, an object of the present invention is to provide a novel apparatus and method for calibrating the contact pressure and frictional force of scrubber brushes against a wafer.

Another object of the present invention is to provide a novel apparatus and method which is capable of promoting optimum post-CMP cleaning of wafers.

Still another object of the present invention is to provide a novel apparatus and method which is capable of preventing excessive scratching of wafers, particularly during post-CMP cleaning of the wafers.

Yet another object of the present invention is to provide a novel brush pressure calibration apparatus and method for correlating the frictional force of adjacent scrubber brushes against respective surfaces of a wafer with the gap distance between the brushes.

A still further object of the present invention is to provide a novel method which includes the placement of a test plate or plates between adjacent scrubber brushes of a scrubber cleaning apparatus and measurement of the frictional force of the brushes against the test plate to determine the correct gap distance between the brushes for optimal scrubbing of production wafers.

Another object of the present invention is to provide a novel brush pressure calibration apparatus and method which facilitates the real-time adjustment of the frictional force of scrubber brushes against a wafer during scrubber cleaning of the wafer.

SUMMARY OF THE INVENTION

In accordance with these and other objects and advantages, the present invention is generally directed to a novel method for calibrating the gap distance between adjacent scrubber brushes in a scrubber cleaning apparatus with the frictional force of the brushes against a wafer during scrubber cleaning of the wafer after a CMP process, for example. The method includes placing at least one test plate between the adjacent scrubber brushes, rotating the scrubber brushes against the test plate or plates, determining the frictional force of each brush against the plate or plates, and adjusting the gap distance between the brushes to obtain a desired frictional force for the scrubber cleaning of production wafers.

In a preferred embodiment, two test plates are placed between the rollers, at respective ends of the scrubber brushes. Accordingly, the frictional force between each test plate and the corresponding end portion of the brushes can be measured. The obtained frictional force can be used to adjust the gap distance, the parallelism, or both the gap distance and the parallelism between the brushes in order to obtain the desired frictional force.

The present invention further includes an apparatus for calibrating the gap distance between scrubber brushes of a scrubber cleaning apparatus with the frictional force of the brushes against a wafer. The apparatus includes a frame on which is provided at least one load cell. A test plate is suspended from each load cell for placement between adjacent scrubber brushes of the scrubber cleaning apparatus. An electronic indicator is operably connected to the load cell or cells to indicate the frictional force of the scrubber brushes, as measured by the load cell or cells, against the test plate or plates as the brushes are rotated against the plate or plates.

BRIEF DESCRIPTION OF THE DRAWINGS

The invention will now be described, by way of example, with reference to the accompanying drawings, in which:

FIG. 6 is a front view of a pair of scrubber brushes being rotated against a test plate according to the method of the present invention;

FIG. 7 is a top view of a pair of scrubber brushes, illustrating adjustment of the parallelism between the brushes according to the present invention; and FIG. 8 is a flow diagram illustrating sequential process steps according to the brush pressure calibration method of the present invention.

DETAILED DESCRIPTION OF THE INVENTION

The present invention is particularly beneficial in the calibration of the gap distance between a pair of scrubber brushes with the frictional force of the brushes exerted against a post-CMP semiconductor wafer substrate in a scrubber cleaning apparatus. However, the invention is more generally applicable to the scrubber cleaning of semiconductor wafer substrates in other phases of IC fabrication. The present invention may further be adapted to the scrubber cleaning of substrates in other industrial applications.

The present invention contemplates a brush pressure calibration apparatus and method which is used to correlate the frictional force of a pair of adjacent scrubber brushes in a brush scrubber apparatus with the gap distance between the scrubber brushes. A schematic of a typical brush scrubber apparatus 74 which is suitable for implementation of the present invention is shown in phantom in FIG. 4 and in solid lines in FIG. 5. The brush scrubber apparatus 74 may be a conventional apparatus such as a MIRRAMESA (trademark) brush scrubber apparatus which is availabe from Applied Materials and is used to remove particles from post-CMP wafers. However, the brush scrubber apparatus 74 may be any type of double-brush scrubber apparatus known by those skilled in the art which is capable of facilitating the simultaneous scrubber cleaning of respective surfaces on a semiconductor wafer substrate. For example, the apparatus and method of the present invention is suitable for use with scrubber cleaning apparatus models including Lam Ontrak, DNS, Ebara 222, AMAT reflexion and Ebara F-Rex300(S).

Figure 1:
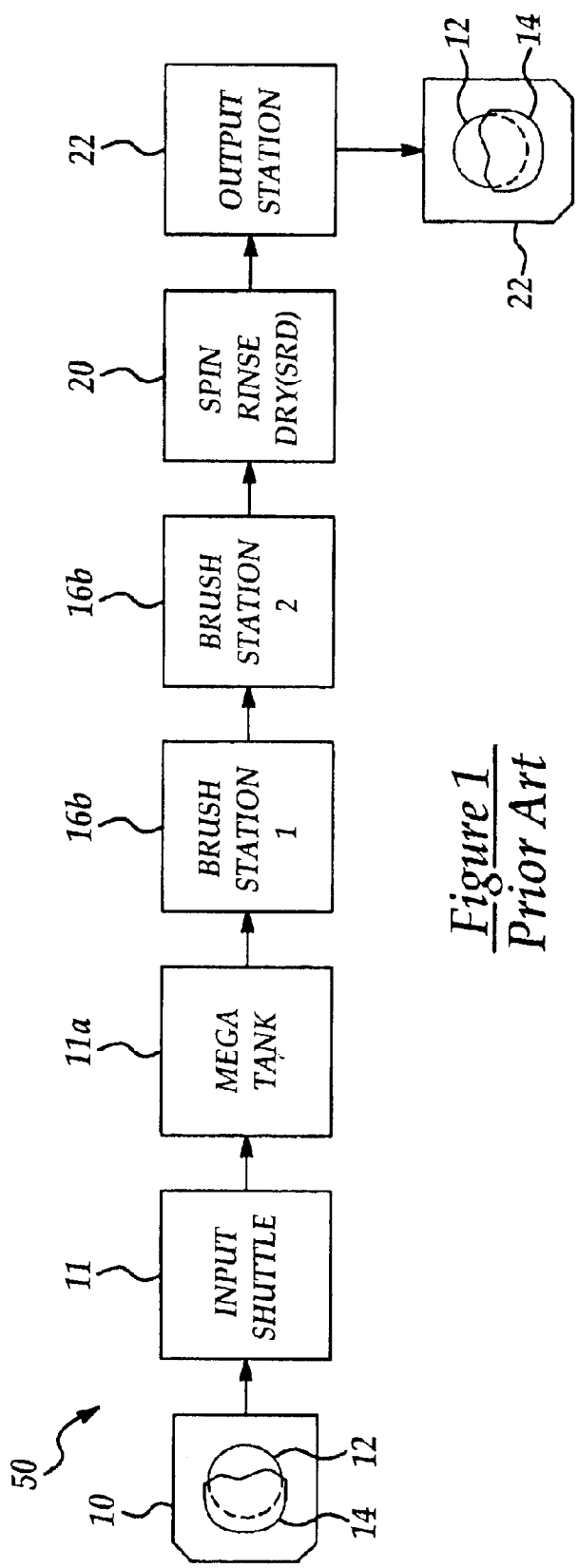
FIG. 1 is a block diagram illustrating a typical conventional post-CMP cleaning sequence of a post-CMP cleaning system for cleaning wafers.
Figure 2:
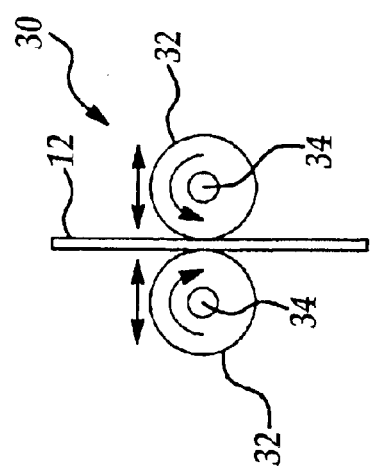
FIG. 2 is a schematic of a pair of scrubber brushes of a conventional brush assembly in a post-CMP cleaning system.
Figure 3A:
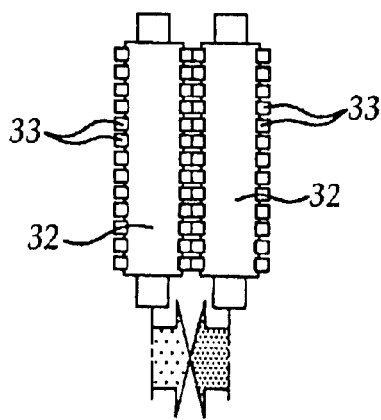
FIGS. 3A and 3B illustrate a typical conventional process for calibrating the contact pressure between scrubber brushes.
Figure 3B:
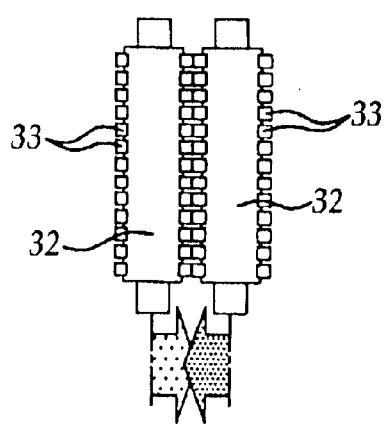
Figure 4:
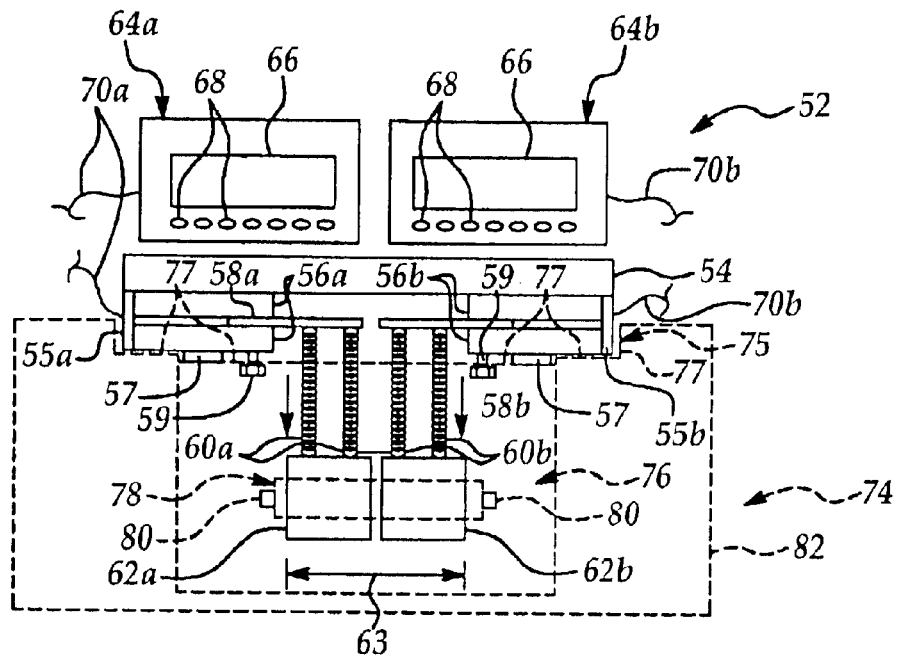
FIG. 4 is a front view, partially schematic, of a brush pressure calibration apparatus of the present invention, mounted on a scrubber cleaning apparatus (in phantom) in operation of the brush pressure calibration apparatus.
Figure 5:
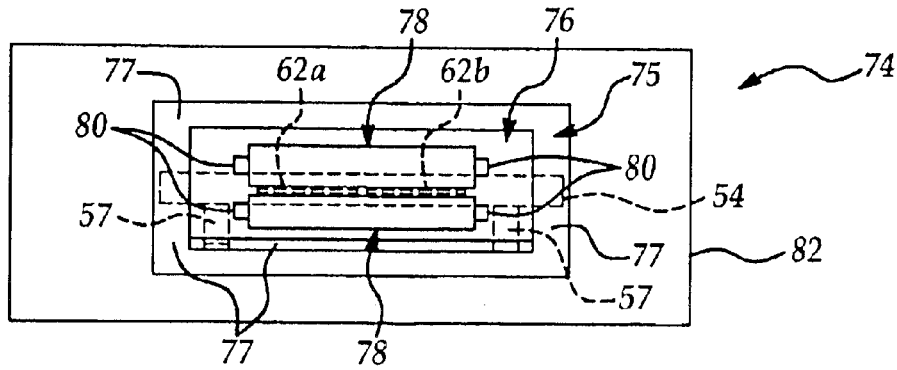
FIG. 5 is a top view, partially schematic, of the brush pressure calibration apparatus (partially in phantom), mounted on a scrubber cleaning apparatus (in solid lines) in operation of the brush pressure calibration apparatus.

As shown in FIGS. 4 and 5, the brush scrubber apparatus 74 typically includes a housing 82 which defines a cleaning interior 76. An opening 75, typically surrounded by a recessed shoulder 77 in the top of the housing 82, communicates with the cleaning interior 76. A pair of horizontal, adjacent scrubber brushes 78, each mounted on a corresponding brush shaft 80, is provided in the cleaning interior 76. In use, the scrubber brushes 80 are rotated by a brush drive motor (not shown) as a wafer (not shown) is placed vertically between the brushes 80 to scrub respective surfaces of the wafer. Water jets (not shown) are simultaneously sprayed against both surfaces of the wafer to wash the particles dislodged by the brushes 80, from the wafer.

Referring again to FIG. 4, an illustrative embodiment of the brush pressure calibration apparatus according to the present invention is generally indicated by reference numeral 52. The brush pressure calibration apparatus 52 includes a generally elongated support frame 54, such as a crossbeam. First and second mount plates 55a, 55b, respectively, are typically bolted or otherwise attached to respective ends of the support frame 54 and extend downwardly therefrom.

A first pair of spaced-apart load cells 56a is typically bolted or otherwise attached to the first mount plate 55a, and a second pair of spaced-apart load cells 56b is typically bolted or otherwise attached to the second mount plate 55b. Each pair of load cells 56a, 56b typically extends generally parallel to the support frame 54. A hard stop screw 59 may engage each pair of load cells 56a. A first elongated suspension arm 58a extends in cantilever fashion from between the first pair of load cells 56a. A second elongated suspension arm 58b likewise extends in cantilever fashion from between the second pair of load cells 56b. The suspension arms 58a, 58b extend horizontally toward each other from the respective pairs of load cells 56a, 56b. The load cells 56a, 56b may be conventional and are capable of sensing the quantity of downward pressure, typically in grams, exerted on each of the suspension arms 58a, 58b, respectively, as hereinafter further described.

A support arm 57 typically extends horizontally from the bottom one of each pair of load cells 56a, 56b. The support arms 57 are adapted to support the frame 54 of the apparatus 52 over the opening 75 in the top of the scrubber clean apparatus 74, as particularly shown in FIG. 5 and hereinafter further described. A first pair of parallel suspension chains 60a is suspended from the first suspension arm 58a. A second pair of parallel suspension chains 60b is suspended from the second suspension arm 58b.

A first generally rectangular test plate 62a is attached to the bottom ends of the first pair of suspension chains 60a. A second generally rectangular test plate 62b is attached to the bottom ends of the second pair of suspension chains 60b. The first test plate 62a and the second test plate 62b are thus suspended adjacent to each other from the respective suspension arms 58a, 58b, in generally coplanar relationship with respect to each other.

Each test plate 62a, 62b has a thickness which is substantially equal to that of semiconductor wafers to be scrubber cleaned in the scrubber clean apparatus 74. Preferably, each test plate 62a, 62b is PMMA (polymethyl methacrylate), although other materials of construction may be used instead. As shown in FIG. 4, the combined plate width 63 of the adjacent test plates 62a, 62b typically corresponds to the width or diameter of wafers to be scrubber cleaned using the scrubber clean apparatus 74. For example, the combined plate width 63 is preferably 300 mm for wafers having a width of 300 mm.

As further shown in FIG. 4, a first electronic indicator 64a is operably connected to the first pair of load cells 56a, typically through suitable wiring 70a, to receive an electronic data signal from the first pair of load cells 56a that corresponds to the downward force exerted on the suspension chains 60a. In similar fashion, a second electronic indicator 64b is operably connected to the second pair of load cells 56b, typically through suitable wiring 70b, to receive an electronic data signal from the second pair of load cells 56b that corresponds to the downward force exerted on the suspension chains 60b. Each of the electronic indicators 64a, 64b may be conventional and includes a digital display 66 and multiple selector buttons 68. In operation of the brush pressure calibration apparatus 52, as hereinafter described, the selector buttons 68 are capable of selecting between various modes including a "frictional force" mode, in which the downward force, typically in grams, exerted on the load cells 56a, 56b by the respective suspension arms 58a, 58b, is displayed in the digital display 66 of the corresponding first indicator 64a and second indicator 64b.

Referring next to FIGS. 6–8B, in conjunction with FIGS. 4 and 5, the brush pressure calibration apparatus and method of the present invention is carried out typically in the following manner. As indicated in step S1 of FIG. 8A, with the scrubber brushes 32 of the scrubber clean apparatus 74 in the "open" position, the first test plate 62a and second test plate 62b are initially placed between the parallel scrubber brushes 32. As shown in FIGS. 4 and 5, the mount plates 55a, 55b and the support arms 57 of the apparatus 52 are supported on the recessed shoulder 77, over the cleaning interior 76 of the scrubber clean apparatus 74. Accordingly, as shown in FIG. 4, the suspension chains 60a, 60b are suspended downwardly through the opening 75, into the cleaning interior 76, with the test plates 62a, 62b disposed in adjacent relationship to each other between the scrubber brushes 78, as shown in FIG. 5.

After the test plates 62a, 62b have been placed between the adjacent scrubber brushes 78, the scrubber brushes 78 are moved from the open position to the closed position by adjusting the "hard stop" (not shown) on the scrubber clean apparatus 74, according to the knowledge of those skilled in the art. Next, as indicated in step S2 and shown in FIG. 6, the scrubber brushes 78 are rotated against the test plates 62a, 62b at a rotational speed of typically about 400 rpm. Accordingly, the brushes 78 exert a downward frictional force 84 against the test plates 62a, 62b. This frictional force 84 exerted against the test plates 62a, 62b corresponds to the downward pressure, typically in grams, exerted on the test plates 62a, 62b.

As indicated in step S3 of FIG. 8A, the frictional force 84 of the brushes 78 against the test plates 62a, 62b is determined. The frictional force 84 exerted on the first test plate 62a is transmitted through the suspension chains 60a to the suspension arm 58a, and from the suspension arm 58a, through the wiring 70a to the electronic indicator 64a. In similar fashion, the frictional force 84 exerted on the second test plate 62b is transmitted through the suspension chains 60b to the suspension arm 58b, and from the suspension arm 58b, through the wiring 70b to the electronic indicator 64b. Thus, the frictional force 84 exerted on the first test plate 62a can be monitored independently of the frictional force 84 exerted on the second test plate 62b.

The frictional force 84 is proportional to the contact pressure of the brushes 78 against the respective surfaces of the test plates 62a, 62b, and is inversely proportional to the gap distance 86 (FIG. 7) between the brushes 78. As the brushes 78 are rotated against the test plates 62a, 62b, the gap distance 86 is typically indicated on a computer screen or other display (not shown) connected to the scrubber clean apparatus 74, in conventional fashion, and varies according to the position of the "hard stop" (not shown) on the control panel of the scrubber clean apparatus 74. Accordingly, as indicated in step S4, the gap distance 86 is adjusted, as needed to obtain the desired frictional force 84 (such as for example, 250 grams), by adjusting the "hard stop" on the apparatus 74. Therefore, as indicated in step S5, the gap distance 86 is correlated with the frictional force 84 which is optimal for the particular post-CMP or other cleaning application to be subsequently carried out on production wafers. The gap distance 86 which is necessary to produce the frictional force 84 for optimal post-CMP or other cleaning typically ranges from about 0.9 mm to about 1.1 mm to obtain a frictional force 84 of from typically about 230 g to typically about 270 g.

After the gap distance 86 has been correlated with the correct frictional force 84 to be used for optimal polishing of production wafers, this gap distance 86 is noted and used to subsequently polish the production wafers. As indicated in step S6, the test plates 62a, 62b are next removed from between the scrubber brushes 78 and the brush pressure calibration apparatus 52 is removed from the scrubber clean apparatus 74. Finally, as indicated in step S6, production wafers (not shown) are scrubbed using the gap distance 86 obtained through steps S1–S5 in order to achieve the frictional force 84 for optimal polishing of the wafers.

Referring next to FIG. 7, it will be appreciated by those skilled in the art that, due to the independent measurements of the frictional forces exerted on the test plates 62a, 62b by the respective ends of the adjacent scrubber brushes 78, the parallelism of the scrubber brushes 78 can be determined. A deviation in the parallelism between the brushes 78 is indicated by a disparity in the frictional forces 84 indicated by the electronic indicators 64a, 64b. Accordingly, by use of the operational controls of the scrubber clean apparatus 74, according to the knowledge of those skilled in the art, the relative positions of the scrubber brushes 78 with respect to each other can be adjusted to provide the same frictional force 84 as measured by both of the electronic indicators 64a, 64b. This would result in a uniform cleaning rate from all regions on the surface of wafers cleaned using the apparatus 74.

While the preferred embodiments of the invention have been described above, it will be recognized and understood that various modifications can be made in the invention and the appended claims are intended to cover all such modifications which may fall within the spirit and scope of the invention.

What is claimed is:

1. A brush pressure calibration apparatus for correlating a gap distance between scrubber brushes with a frictional force of the scrubber brushes, comprising:
   a support frame;
   at least one pair of load cells carried by said support frame;
   at least one test plate operably engaging said at least one pair of load cells for exerting pressure against said at least one pair of load cells; and
   at least one electronic indicator operably connected to said at least one pair of load cells, respectively, for indicating a force exerted on said at least one pair of load cells by said at least one test plate.

2. The apparatus of claim 1 wherein:
   said at least one pair of load cells comprises a first pair of load cells and a second pair of load cells carried by said support frame;
   said at least one test plate comprises a first test plate and a second test plate operably engaging said first pair of load cells and said second pair of load cells, respectively; and
   said at least one electronic indicator comprises a first electronic indicator operably connected to said first pair of load cells and a second electronic indicator operably connected to said second pair of load cells.

3. The apparatus of claim 1 wherein said at least one test plate comprises polymethyl methacrylate.

4. The apparatus of claim 3 wherein:
   said at least one pair of load cells comprises a first pair of load cells and a second pair of load cells carried by said support frame;
   said at least one test plate comprises a first test plate and a second test plate operably engaging said first pair of load cells and said second pair of load cells, respectively; and
   said at least one electronic indicator comprises a first electronic indicator operably connected to said first pair of load cells and a second electronic indicator operably connected to said second pair of load cells.

5. The apparatus of claim 1 further comprising at least one suspension arm engaging said at least one pair of load cells, respectively, and at least one pair of suspension chains carried by said at least one suspension arm, respectively; and wherein said at least one test plate is carried by said at least one pair of suspension chains, respectively.

6. The apparatus of claim 5 wherein:
   said at least one pair of load cells comprises a first pair of load cells and a second pair of load cells carried by said support frame;
   said at least one suspension arm comprises a first suspension arm and a second suspension arm engaging said first pair of load cells and said second pair of load cells, respectively;
   said at least one pair of suspension chains comprises a first pair of suspension chains and a second pair of suspension chains carried by said first suspension arm and said second suspension arm, respectively;

said at least one test plate comprises a first test plate carried by said first pair of suspension chains and a second test plate carried by said second pair of suspension chains; and said at least one electronic indicator comprises a first electronic indicator operably connected to said first pair of load cells and a second electronic indicator operably connected to said second pair of load cells.

7. The apparatus of claim 5 wherein said at least one test plate comprises polymethyl methacrylate.

8. The apparatus of claim 7 wherein:

said at least one pair of load cells comprises a first pair of load cells and a second pair of load cells carried by said support frame;

said at least one suspension arm comprises a first suspension arm and a second suspension arm engaging said first pair of load cells and said second pair of load cells, respectively;

said at least one pair of suspension chains comprises a first pair of suspension chains and a second pair of suspension chains carried by said first suspension arm and said second suspension arm, respectively;

said at least one test plate comprises a first test plate carried by said first pair of suspension chains and a second test plate carried by said second pair of suspension chains; and said at least one electronic indicator comprises a first electronic indicator operably connected to said first pair of load cells and a second electronic indicator operably connected to said second pair of load cells.

9. A method of correlating a frictional force of a pair of scrubber brushes with a gap distance between the brushes, comprising the steps of:

providing at least one test plate;

placing said at least one test plate between the brushes;

rotating the brushes against said at least one test plate;

measuring the frictional force exerted by the brushes against said at least one test plate; and correlating the frictional force with the gap distance between the brushes.

10. The method of claim 9 wherein said rotating the brushes against said at least one test plate comprises rotating the brushes against said at least one test plate at a rotational speed of about 400 rpm.

11. The method of claim 9 further comprising the steps of:

providing at least one pair of load cells;

operably connecting said at least one test plate to said at least one pair of load cells, respectively;

providing at least one indicator;

operably connecting said at least one pair of load cells to said at least one indicator, respectively; and indicating the frictional force on said at least one indicator.

12. The method of claim 11 wherein said rotating the brushes against said at least one test plate comprises rotating the brushes against said at least one test plate at a rotational speed of about 400 rpm.

13. The method of claim 9 wherein said at least one test plate comprises polymethyl methacrylate.

14. The method of claim 13 wherein said rotating the brushes against said at least one test plate comprises rotating the brushes against said at least one test plate at a rotational speed of about 400 rpm.

15. The method of claim 13 further comprising the steps of:

providing at least one pair of load cells;

operably connecting said at least one test plate to said at least one pair of load cells, respectively;

providing at least one indicator;

operably connecting said at least one pair of load cells to said at least one indicator, respectively; and indicating the frictional force on said at least one indicator.

16. The method of claim 15 wherein said rotating the brushes against said at least one test plate comprises rotating the brushes against said at least one test plate at a rotational speed of about 400 rpm.

17. A method of correlating frictional forces between a pair of scrubber brushes with a gap distance between the brushes and determining a degree of parallelism between the brushes, comprising the steps of:

providing a pair of test plates;

placing said pair of test plates between the brushes;

rotating the brushes against said pair of test plates;

measuring the frictional forces exerted by the brushes against said pair of test plates, respectively; and correlating the frictional forces with the gap distance and the degree of parallelism between the brushes.

18. The method of claim 17 wherein said rotating the brushes against said pair of test plates comprises rotating the brushes against said pair of test plates at a rotational speed of about 400 rpm.

19. The method of claim 17 further comprising the steps of:

providing two pairs of load cells;

operably connecting said pair of test plates to said pairs of load cells, respectively;

providing a pair of indicators;

operably connecting said pair of load cells to said pair of indicators, respectively; and displaying on said pair of indicators frictional forces exerted by the brushes on said pair of test plates, respectively.

20. The method of claim 19 wherein said rotating the brushes against said pair of test plates comprises rotating the brushes against said pair of test plates at a rotational speed of about 400 rpm.

* * * * *